(12) United States Patent
Ossowski

(10) Patent No.: US 6,228,345 B1
(45) Date of Patent: May 8, 2001

(54) IN VIVO ASSAY FOR INTRAVASATION

(75) Inventor: Liliana Ossowski, Queens, NY (US)

(73) Assignee: Mount Sinai School of Medicine of New York University, New York, NY (US)

( * ) Notice: Subject to any disclaimer, the term of this patent is extended or adjusted under 35 U.S.C. 154(b) by 0 days.

(21) Appl. No.: 09/366,840

(22) Filed: Aug. 4, 1999

(51) Int. Cl.[7] ............................. C12Q 1/68; A61K 49/00
(52) U.S. Cl. ................................. 424/9.1; 424/9.2; 435/6; 435/91.2
(58) Field of Search .................. 435/6, 91.2; 424/93.1, 424/94.1, 9.1, 9.2; 514/44

(56) References Cited

PUBLICATIONS

Poste, G et al., 1980, Cancer Research 40:1636–1644.
Ossowski, L., 1988, Cell 52:321–328.
Chambers, AF et al., 1992, *Journal of the National Cancer Institute* 84:797–803.
Endo, Y et al., 1990, *Jpn. J. Cancer Res.* 81:723–726.
Tsuchiya, Y et al., *Cancer Research* 53:1397–1402, 1993.
Lee et al., 1993, *J Juzen Med Soc.* 102:10–16.
Koop et al., 1994, *Cancer Research* 54:4791–4797.
Uchibayashi T et al., 1994, *Cancer Chemother Pharmacol* 35 Suppl:S84–7.
Koop S., et al, 1996, Proc. Natl. Acad. Sci USA 93:11080–11084.
Yamamoto, H., et al., 1996, Anticancer Research 16:413–418.
Shioda T, et al., 1997, American Journal of Pathology 150:20992112.
Andresen PA et al., Int. J. Cancer 72:1–22, 1997.
Kim J., et al., 1998, Cell 94:353–362.
Quigley JP., et al., 1998, Cell 94:281–284.
Sikorski R et al., 1998, Science 281.
Ossowski, "Plasminogen Activator Dependent Pathways in the Dissemination of Human Tumor Cells in the Chicken Embryo", Cell, vol. 52, p 321–328, Feb. 1998.*
Kim et al. "Requirement for specific proteases in cancer cell intraversation as revealed by a novel semiquantitative PCR–based assay" Cell, vol. 94, p 353–362, Aug. 1998.*
Quigley et al. "Tumor cell intravasation Alu–cidated: The chick embryo opens the window" Cell vol. 94, 281–284, Aug. 1998.*
Anderson "Human gene therapy" Native vol. 392 (supp) p 25–30, Apr. 1998.*
Verma et al. Gene therapy–prblems and prospects Nature, vol. 389, p 239–242, Sep. 1997.*
Orkin et al. "Report and recommendations of the panel to assess the NIH investment in research on gene therapy" p 1–41, Dec. 1995.*
Lee "Antitumor effects of anticancer agents and tumor necrosis factor in conbination with/without hyperthermia on metastasized human bladder cancer cells in chick embryos" Kanazawa Daigaku Juzen Igakkai Zasshi, 102(1), p 10–16, 1993.*

* cited by examiner

Primary Examiner—Robert A. Schwartzman
Assistant Examiner—Karen A. Lacourciere

(57) ABSTRACT

The present invention relates to a novel in vivo assay for quantitating intravasation of cancer cells based on a highly sensitive polymerase chain reaction (PCR) utilized in combination with a chick embryo chorioallantoic membrane (CAM) assay. The assay of the invention provides a method for measuring the metastatic potential of cancer cells. The assay also provides a drug screening assay for identification of agents having anti-metastatic activity.

9 Claims, 14 Drawing Sheets

IN VIVO ASSAY FOR INTRAVASATION

Figure 1:
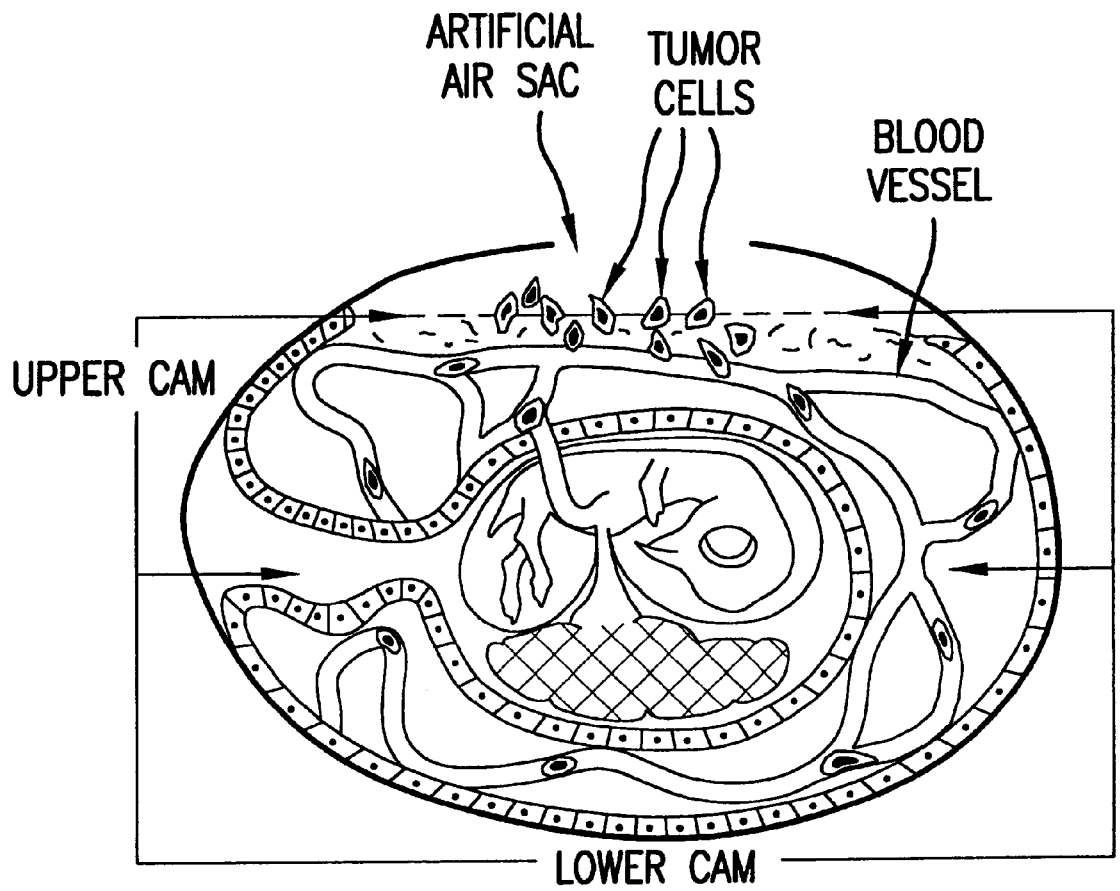

This invention was made with government support under Grant # RO1CA 40758 awarded by the National Institutes for Health. The government has certain rights in this invention.

1. INTRODUCTION

The present invention relates to a novel in vivo assay for quantitating intravasation of cancer cells based on a highly sensitive polymerase chain reaction (PCR) utilized in combination with a chick embryo chorioallantoic membrane (CAM) assay. The assay of the invention provides a method for measuring the metastatic potential of cancer cells. The assay also provides a drug screening assay for identification of agents having anti-metastatic activity. The present invention is based on the discovery that when cancer cells are inoculated onto the CAM of a chick embryo, the ability of cancer cells to invade blood vessels can be measured using a sensitive PCR based assay. In addition, blood vessel intravasation by cancer cells was significantly inhibited when agents such as metalloproteinase inhibitors were co-inoculated with the cancer cells.

2. BACKGROUND OF THE INVENTION

The spread of cancer cells from a primary tumor to a site of metastasis formation involves multiple interactions such as invasion of extracellular matrix, neovascularization, invasion of the blood vessel wall (intravasation), exit from the circulation (extravasation) and establishment of secondary growth. Because cancer cells reach distant sites by disseminating through blood or lymphatic circulation, breaching of the vascular wall is a crucial event in metastasis formation. It is not known how early in disease progression cancer cells acquire the ability to intravasate. However, once established, this pathway appears to remain active as cancer cells can be detected in repeated blood samples of cancer patients.

Escape of cancer cells from the circulation, referred to as extravasation, is thought to be a major rate-limiting step in metastasis, with few cells being able to extravasate. However, highly metastatic cells are believed to extravasate more readily than poorly metastatic cells. A number of studies designed to assess metastasis by measuring extravasation have been performed using a chick embryo chorial-lantoic membrane (CAM) model system in which a large number of cancer cells are injected directly into the chorioallantoic membrane vein (Koop et al., 1994, Cancer Research 54:4791–4797; Chambers et al., 1997, J. Nat'l Cancer Inst. 84:797–803; Tsuchiya et al., 1993, Cancer Research 53:1397–1402; Shioda et al., 1997, AJP 150:2099–2112; Endo et al., 1990, J. Cancer Res. 81:723–6; Yamamoto et al., 1996, Anticancer Res. 16:413–7; Tsuchiya et al., Int. J. Cancer 56:46–51). However, since cancer cells are injected directly into the blood vessel, such studies fail to assay a tumor cell's ability to invade blood vessel walls (intravasation), a defect that would severely diminish the number of cancer cells delivered into the circulation and reduce the chances of metastatic growth.

While many aspects of cancer dissemination have been extensively studied, very little biochemical information related to the process of intravasation, i.e., the invasion of the blood vessel wall, is available. This may be in part due to the paucity of experimental models capable of mimicking the cellular and molecular interactions required for successful completion of intravasation. Existing models, such as mouse bladder (Poste et al., 1980 Cancer Res. 40:1636–1644) or human amnion denuded of epithelium and re-seeded with endothelial cells (Foltz et al., 1982, In "*Interaction of Platelets and Tumor Cells*", G. A. Jamieson, (ed.), New York: Alan R. Liss, Inc. pp. 353–371), are used infrequently because they recapitulate poorly the structure of blood vessels and in particular, small vessels such as capillaries and post-capillary venules, where most of the cancer cell invasion is believed to take place. The scarcity of "spontaneously" metastasizing human tumors in experimental animals is another obstacle to the study of intravasation. The reason for the inefficient "spontaneous" metastasis is not understood.

To identify properties that define cells capable of successful intravasation, and to screen for compounds capable of inhibiting metastic growth, it is imperative that quantitative in vivo assays are developed in which intravasation can be measured.

3. SUMMARY OF THE INVENTION

The present invention relates to a novel in vivo assay for quantitating the ability of cancer cells to breach blood vessel walls based on a highly sensitive PCR amplification step used in combination with a chick embryo CAM assay. The assay of the invention provides a method for quantitating the metastatic potential of a cancer cell. The invention further relates to the use of the in vivo assay to screen for agents capable of inhibiting intravasation, and thereby modulating the metastatic potential of cancer cells. The assay of the invention has the advantage of providing a highly sensitive assay system capable of mimicking the in vivo cellular and molecular interactions required for successful completion of intravasation.

The assay of the invention involves the use of a chick embryo CAM model system for measuring intravasation. The assay of the invention comprises the inoculation of tumor cells onto the "upper" chorioallantoic membrane ("upper" CAM) of an artificially created air sac in a chick embryo; and the subsequent detection and quantitation of cancer cells that have entered the vasculature and migrated into the "lower" chorioallantoic membrane ("lower CAM") of the embryo using PCR amplification of inoculated cell-specific DNA sequences. The presence of cancer cell specific DNA sequences in the lower CAM of the embryo, as detected by PCR, indicates that the inoculated cancer cells are capable of invading intact blood vessel walls, disseminating, and arresting in small blood vessels of the chick embryo tissues such as those located in the lower CAM.

Further, the assay of the invention can be used to screen for agents capable of inhibiting cancer cell intravasation. In assays designed to identify agents with the potential for inhibiting metastasis, a test agent is included with the inoculated cancer cells or injected into the vasculature of the chick embryo. The assay of the invention may also be used to detect phenotypic changes effected by genetic manipulation of cancer cells that results in changes in metastatic potential. The assay can be used in conjunction with new gene discovery methods to test the role of newly discovered genes in control of metastasis.

The invention is based on the observation that when cancer cells are inoculated onto the upper chorioallantoic membrane CAM of the chick embryo, the cells are capable of invading blood vessel walls and migrating to different regions of the embryo as detected by PCR amplification of cancer cell specific DNA sequences. It was further demonstrated that intravasation was inhibited by 90% when the cancer cells were co-inoculated with the metalloproteinase inhibitor, marimastat. In addition, recombinant expression of antisense uPAR in cancer cells inhibited intravasation by 50%–70%.

4. BRIEF DESCRIPTION OF THE DRAWINGS

FIG. 1. Scheme of the Intravasation Assay. Generation of an artificial air sac results in a wound to the epithelium and basement membrane lining the "upper CAM". This area is used to inoculate tumor cell suspensions or tumor fragments which can enter the vascular stroma of the CAM regardless of their invasive potential (Ossowski, 1988, Cell Biol. 107:2437–2445). Cells that can penetrate blood vessel walls circulate and arrest in vessels of embryonic and extra-embryonic tissues. To quantitate tumor cells entrapped in the ventral "lower CAM", the egg is cut along the long circumference and the upper half (with the inoculum) is discarded. The content of the lower half of the egg is also discarded, the CAM which lines the cavity of the egg shell is lifted and snap-frozen, genomic DNA is extracted and used as a template for human Alu-sequence amplification by PCR.

Figure 2A:
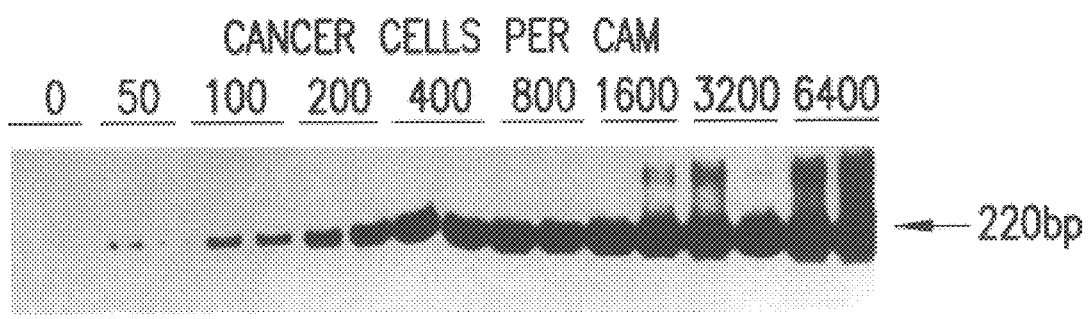
Figure 2B:
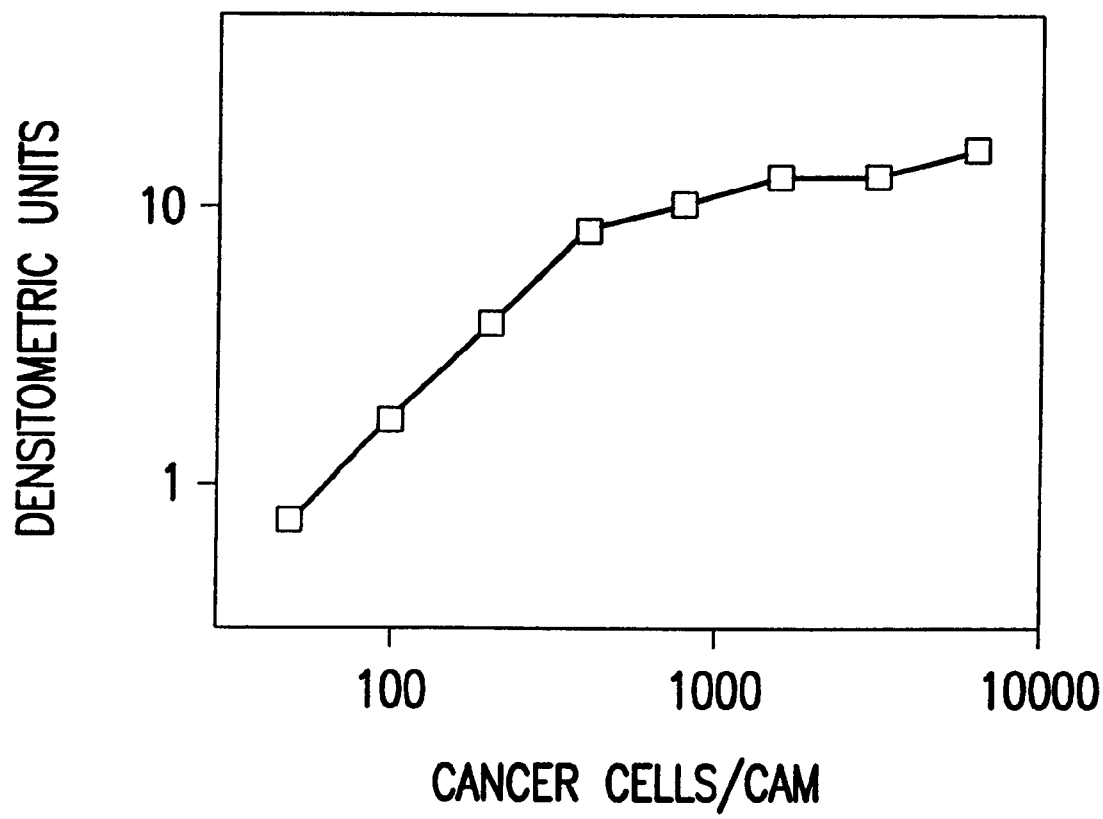

FIGS. 2A–B. PCR Amplification of Alu Sequences in a Mixture of Human and Chicken CAM DNA. FIG. 2A. Genomic DNA was extracted from lower CAMs and mixed with DNA equivalent of 0 to 6,400 HEp3 cells. One microgram aliquots (in duplicate) of the DNAs were used to PCR amplify human Alu sequences in the presence of $^3$P-dCTP and were analyzed by PAGE and autoradiography. The intensity of the ~220 bp band increased with increased content of human cancer cells. FIG. 2B. Individual amplified bands were scanned by densitometer and the values plotted as a function of human cell number equivalent added to the CAMs. The band intensity is directly proportional to cell number over at least a 10 fold range.

Figure 3:
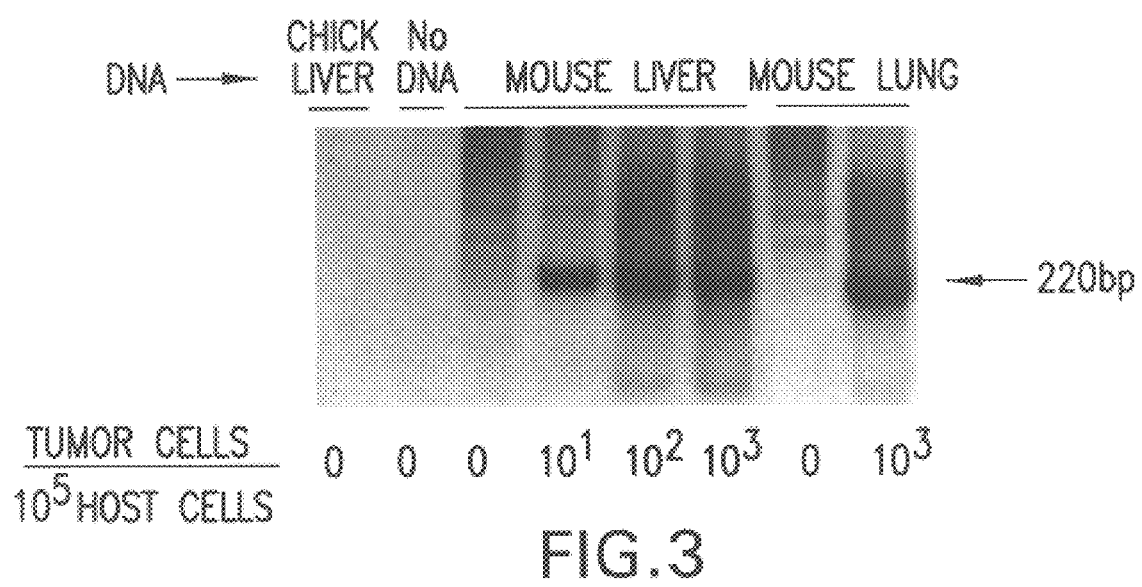

FIG. 3. PCR Amplification of DNA of Human Tumor Cells Mixed with Mouse Tissues. DNA extracted from nude mouse liver or lung was mixed with DNA extracted from HEp3 cells at a ratio of tumor to mouse cells indicated in the figure. Aliquots of 1 µg of genomic DNA were used as templates for PCR amplification. Although mouse DNA produced some background amplification, it is possible to discern and scan the specific, 220 bp human Alu bands. Human DNA can also be detected in rat DNA mixtures using PCR amplification.

Figure 4A:
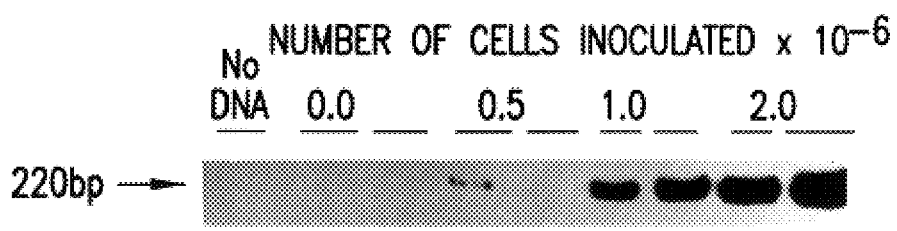
Figure 4C:
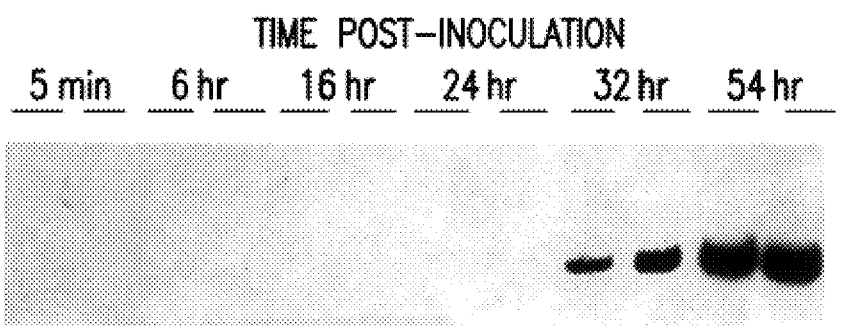
Figure 4D:
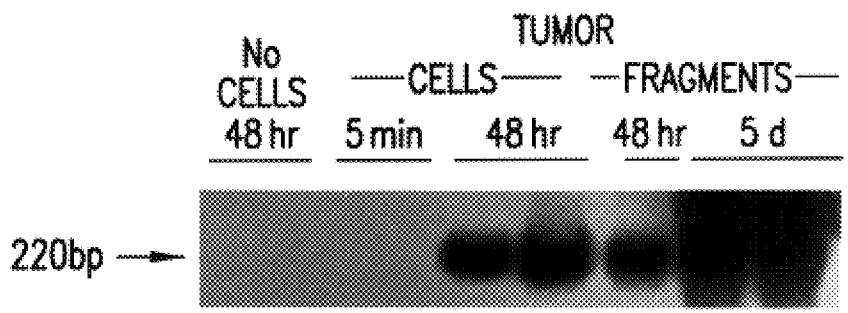
Figure 4B:
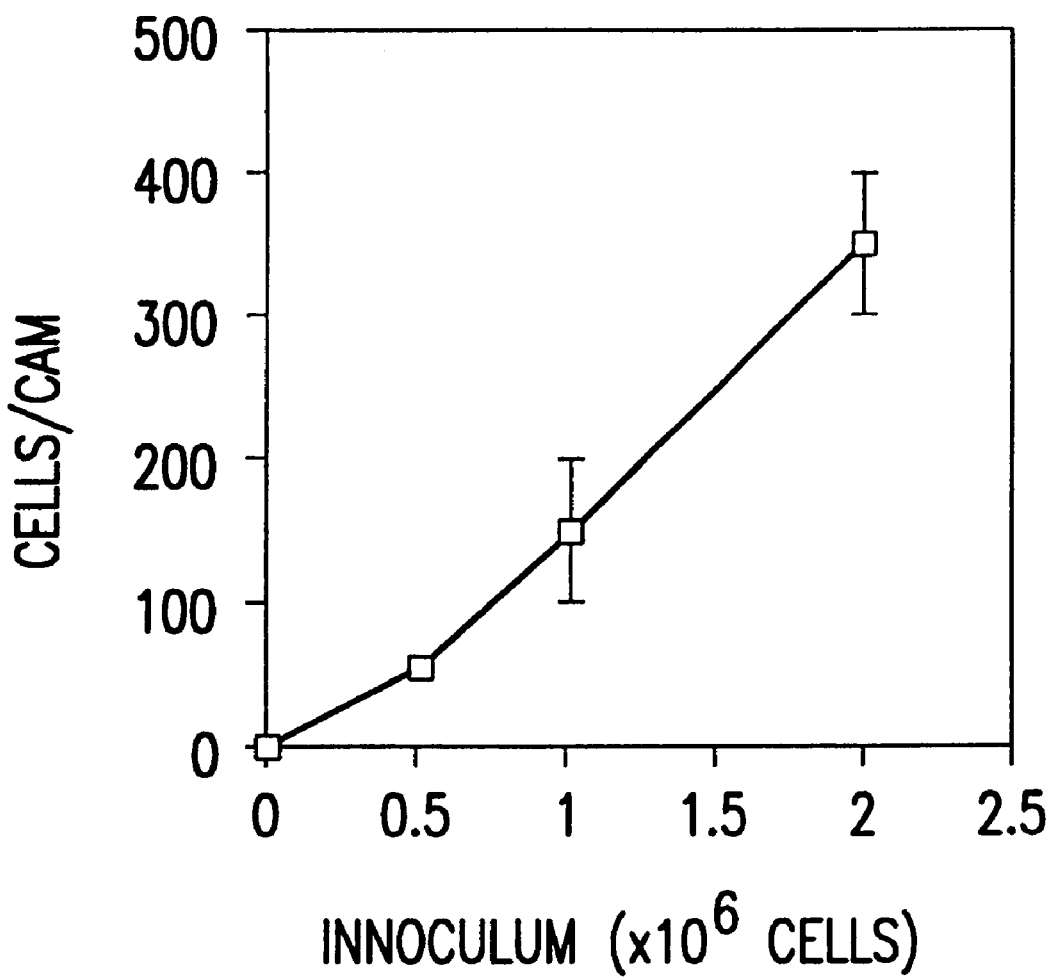

FIGS. 4A–D. Dose and Time Dependence of Intravasation as Measured by Alu-PCR. FIG. 4A. HEp3 cells isolated from tumors and grown in culture were inoculated on CAMs (designated as 0.5, 1.0 and 2.0×10$^6$ cells, respectively). Fifty hours after inoculation, the lower CAMs were excised, and human Alu sequences were amplified. FIG. 4B. Amplified bands shown in 4A were scanned, and the numbers of cancer cells were calculated by extrapolation from the plot shown in FIG. 2B. (The bars are range of the two values). Note the linear ratio between the size of the inoculum and the number of intravasated cells. FIG. 4C. Lower CAMs were excised at the indicated times post-inoculation. No intravasated cells were detected in lower CAMs up to 32 hr post-inoculation indicating that intravasation is an active process. FIG. 4D. Single cells suspensions of HEp3 cells (1×10$^6$/CAM designated Cells) and tumor fragments (several ~2 mm$^2$ HEp3 CAM tumor fragments, calculated to contain a total of ~1×10$^6$ tumor cells) were inoculated on CAMs, and the DNAs of the lower CAMs were extracted and analyzed at the indicated times.

Figure 5A:
Figure 5B:
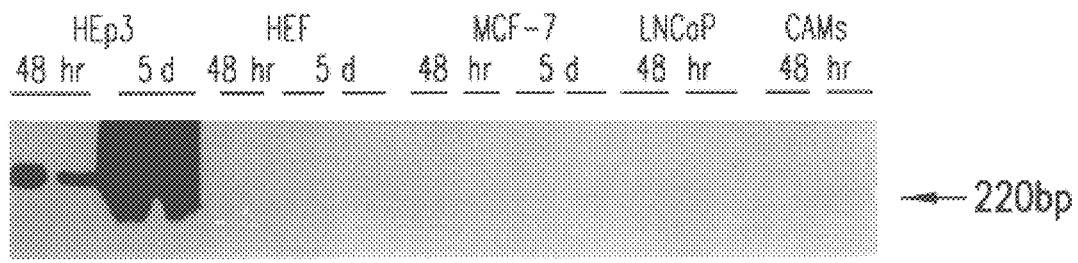

FIGS. 5A–B. Intravasation of Cells With Unequal Malignant Potential. FIG. 5A. Human cell lines capable of producing invasive and/or metastatic tumors in animals: MDA231 is MDAMB231, an estrogen receptor negative breast carcinoma, inoculum 2×10$^6$ cells/CAM; HEp3 is an epidermoid carcinoma, inoculum 1×10$^6$; HT1080 is a fibrosarcoma, HT1080-1, inoculum 1×10$^6$ cells/CAM, HT1080-2, inoculum 2×10$^6$ cells/CAM; PC3, an androgen receptor negative prostate carcinoma, inoculum 2×10$^6$ cells/ CAM. CAMs, DNA from uninoculated CAMs; Pos. Cont., a mixture of CAM and human DNA representing 800 human cells per CAM. The experiment was terminated at 54 hr. Intravasation by all three cells types was repeated at least three times and evaluated by the Alu PCR assay, with similar results. FIG. 5B. Human cells of lesser malignant potential or normal primary fibroblasts. HEp3 (1×10$^6$) was used as a positive control; HEF are human embryo fibroblasts, 7$^{th}$ passage in culture; MCF-7 is an estrogen receptor positive breast cancer cell line; LNCaP is an androgen dependent prostate cancer cell line; CAMs, DNA from uninoculated CAMs. All cells (except HEp3) were inoculated at 2×10$^6$ cells per CAM. The experiment was repeated twice with similar results.

Figure 6:
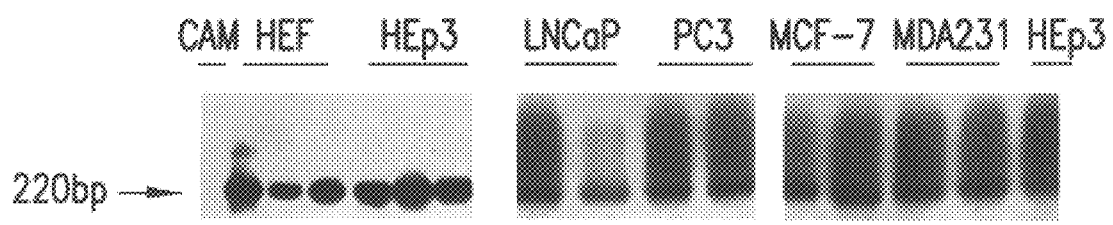

FIG. 6. Arrest of Cells in Lower CAMs After Intravenous Injection. Cells (2×10$^5$ or less) were resuspended in 50 µl PBS and injected into a blood vessel of the upper CAM of 10.5 day old embryos. The lower CAMs were collected 4 hrs after injection and analyzed by the Alu PCR assay.

Figure 7:
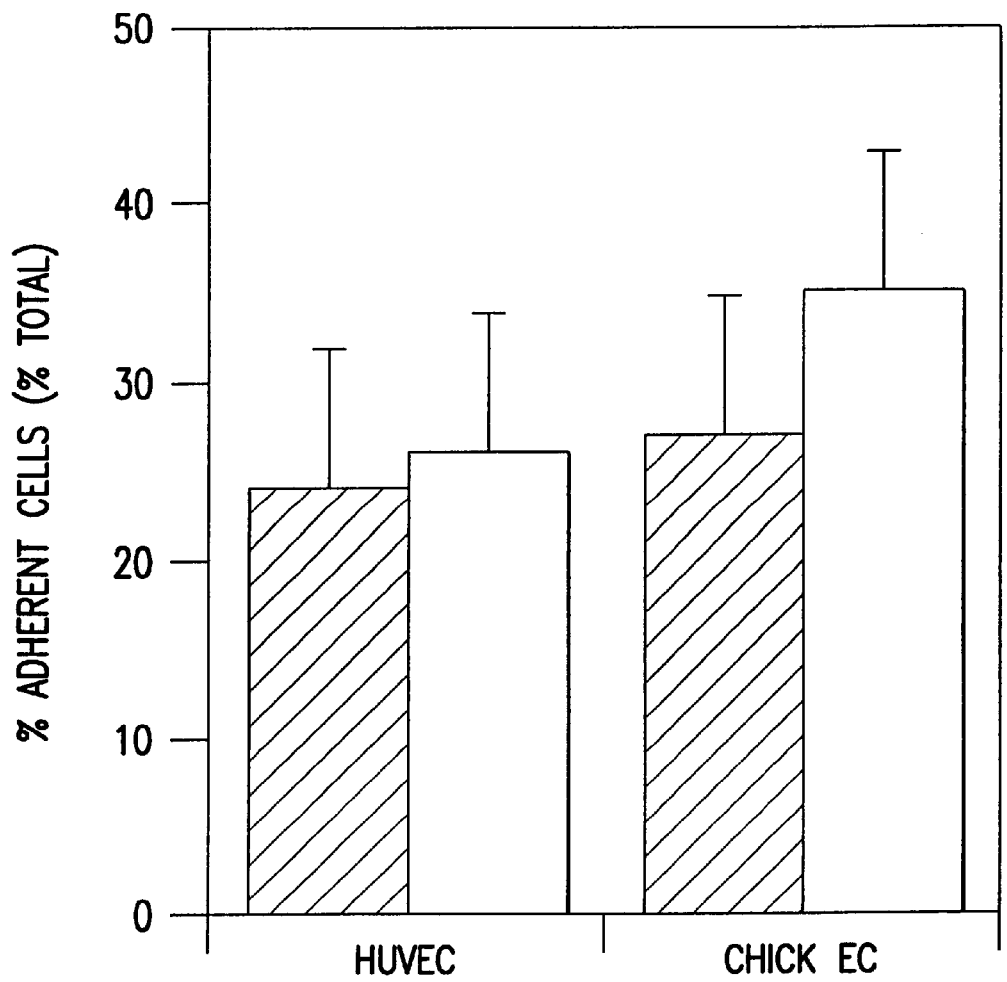

FIG. 7. Attachment of HEp3 Cells to Human HUVEC and Chicken Large Vessel Endothelium. HEp3 cells and their non-malignant derivative were inoculated (1.0×10$^4$cells per well), onto a 24-well tray previously seeded with confluent HUVEC or chicken endothelium, and, to mimic shearing stress in the circulation, the trays were rotated at 60 rpm in a 37° C. incubator. The number of cells adhering after 10 min was determined. The values shown are mean of four determinations; the bars show standard deviation. The darker columns correspond to HEp3 cells; the lighter to the non-malignant HEp3 derivative.

Figure 8:
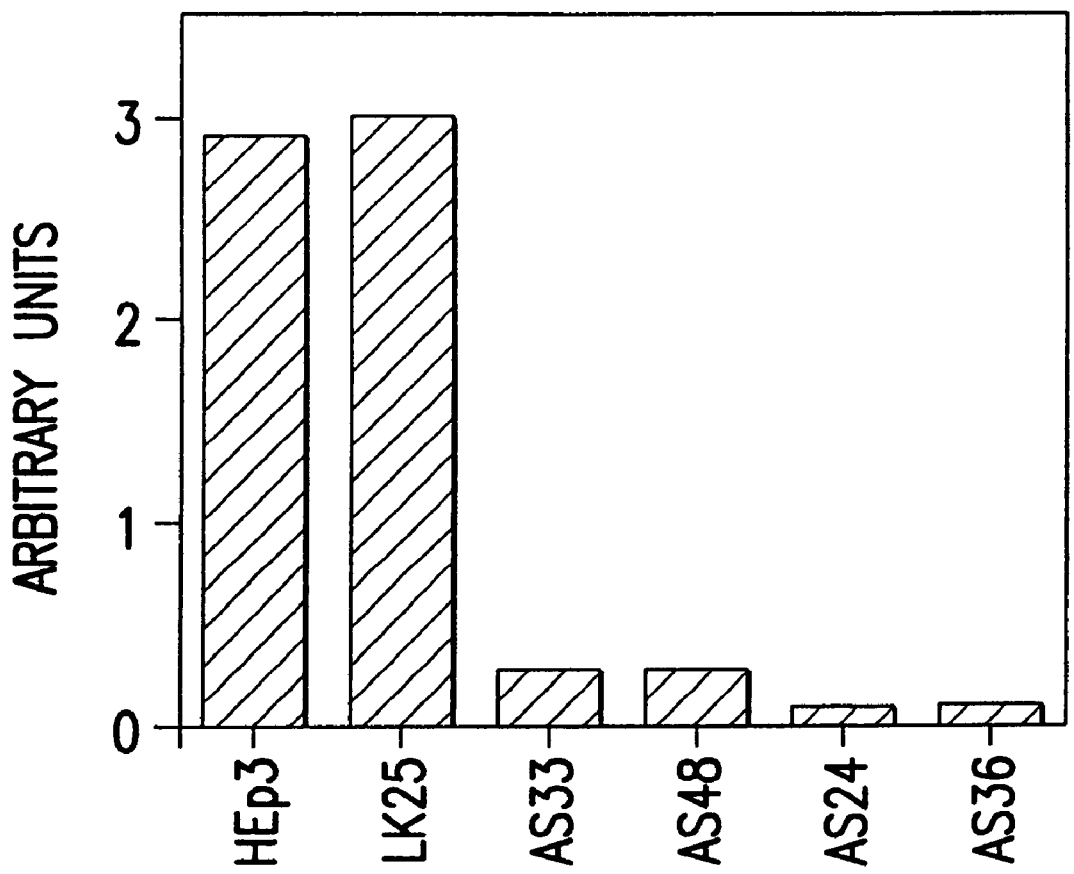

FIG. 8. Intravasation of Cells with Reduced Surface uPAR but Unaltered MMP Production. HEp3 cells (parental) or clones selected from HEp3 cells transfected with vector alone (LK 25) or with vector expressing uPAR-antisense RNA under β-actin promoter (AS33, AS48, AS24 and AS36) in which surface uPAR reduced by more than 50%, were maintained in vivo and used to prepare single cell suspension. (Weights of tumors used to prepare cells for this experiment were as follows: HEp3, 200 mg; LK 25, 170 mg; AS33, 160 mg; AS24, 90 mg; AS36, 150 mg. After 5 days of growth in culture, the cells were detached with EDTA, resuspended at 1×10$^6$ per 50 µl, and used to inoculate duplicate CAMs. At 50 hr after inoculation, the CAMs were processed for determination of intravasated cells. The Alu-PCR-amplified bands were scanned by densitometer, and units obtained for each band are shown. The experiment was repeated three times with essentially similar results.

Figure 9:
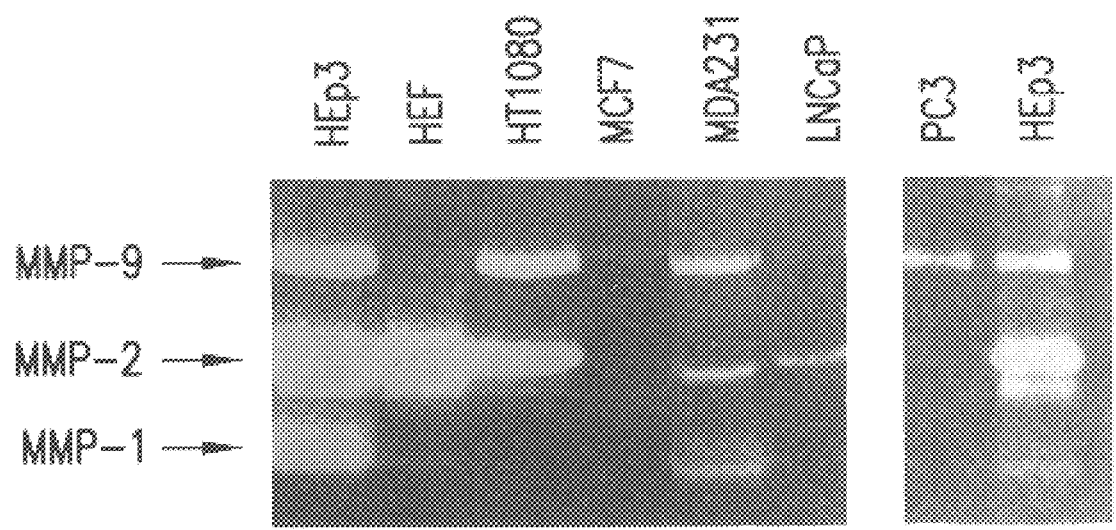

FIG. 9. Secretion of MMPs by Cells Used in Intravasation Assay. Cells were grown in 60 mm dishes until 70% confluence, washed and incubated in serum-free medium for 24 hrs. The media were collected, centrifuged to remove floating cells and debris and 10 µl were of each was analyzed by zymography. Left and right panels show individual experiments.

Figure 10:
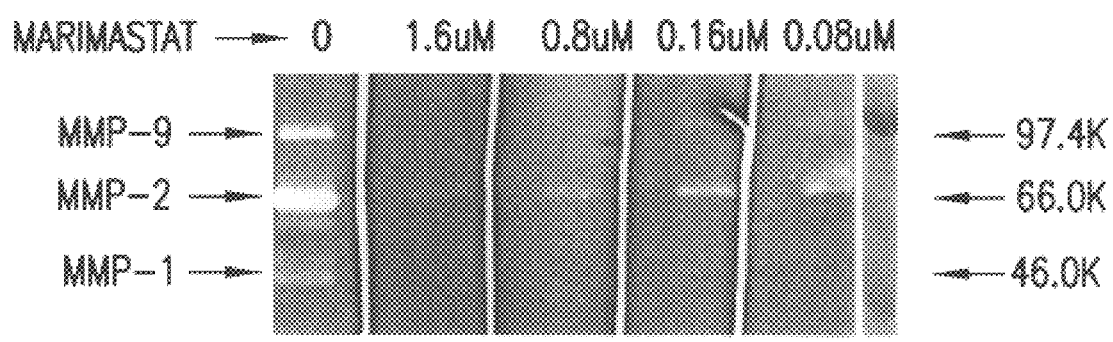

FIG. 10. In Vitro Inhibition of MMP Activity by Marimastat (BB 2516). Serum-free conditioned medium of HEp3 cells was collected and electrophoresed on PAGE by loading 10 µl into each of five wells. The gel was sliced to include one sample per slice and each slice was incubated with marimastat at the indicated concentrations (0–1.6 µM) and the gels were incubated only for 22 hr. MMP-2 activity was not completely inhibited even at the highest concentration tested.

Figure 11:
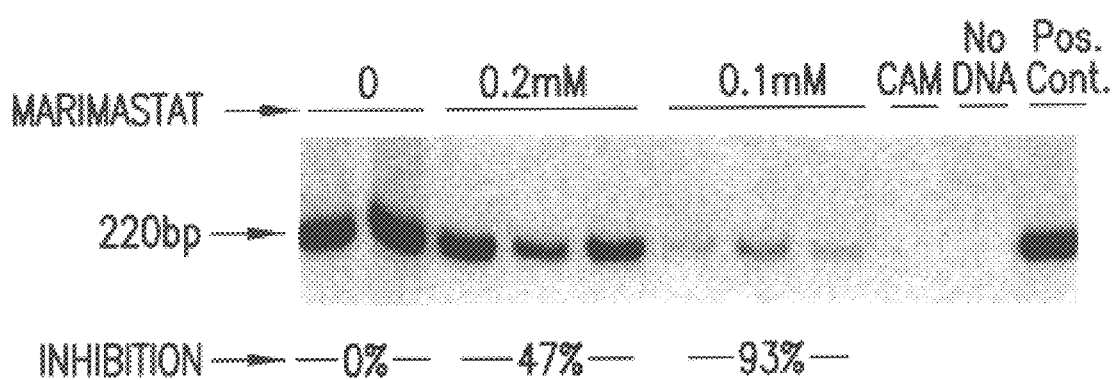

FIG. 11. Inhibition of Intravasation by Marimastat. HEp3 cells (1×10⁶) were suspended in 50 µl PBS without or with 0.1 or 0.2 mM marimastat, and inoculated in triplicate on upper CAM inside a Teflon ring. 24 hr after inoculation, the embryo received a second dose of marimastat, and at 50 hrs post-inoculation, the human DNA content of the lower CAMs (intravasated cells) was measured.

Figure 12:
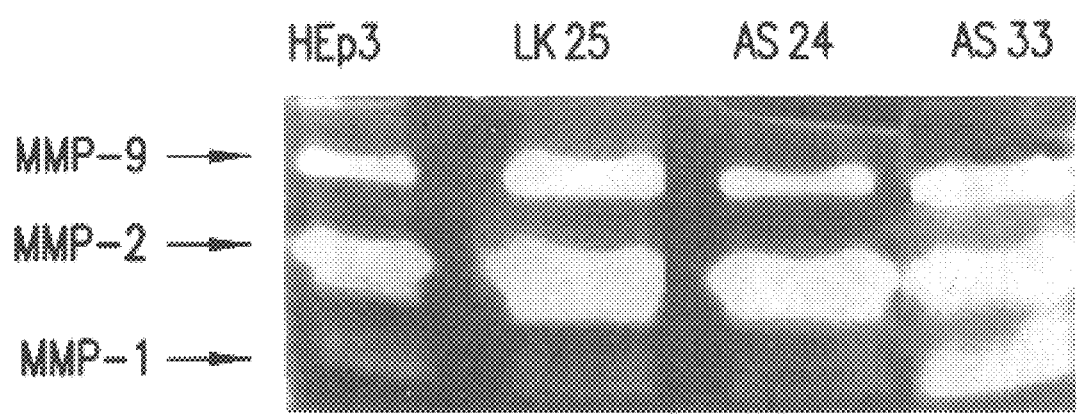

FIG. 12. MMPs Activity in Conditioned Media of HEp3 Cells With Normal or Reduced Surface-uPAR. Parallel cultures of cells tested for intravasation as shown in FIG. 8, were grown until confluence, and used to prepare serum-free conditioned media. The activity was assayed by zymography.

5. DETAILED DESCRIPTION OF THE INVENTION

The invention described in the subsections below relates to a novel highly sensitive in vivo assay for measuring the metastatic potential of cancer cells. In particular, an assay is described that utilizes a chick embryo CAM model system in conjunction with PCR amplification for detection of cancer cell intravasation. The key features of the assay include its sensitivity and its applicability to any established cancer cell line or tumor explant. The in vivo assay system of the invention further provides a screening method for identifying agents with anti-metastatic activity. Such agents may be used to inhibit metastatic spread of cancer cells in subjects having cancer. In addition, the assay may be used to screen for nucleic acid molecules with anti-metastatic potential. For example, antisense molecules may be screened for their ability to inhibit metastasis. In such instances, the nucleic acid molecules to be tested may be introduced into cancer cells followed by inoculation into the upper CAM.

5.1. In Vivo Assay for Measuring the Metastatic Potential of Cancer Cells

The present invention relates to a novel in vivo assay for quantitating the metastatic potential of cancer cells. The assay of the invention involves the use of a chick embryo CAM model assay system in conjunction with PCR amplification. The assay of the invention comprises the inoculation of tumor cells into the "upper" CAM of an artificially created air sac in the chick embryo; and the subsequent detection and quantitation of intravasated cancer cells into the "lower CAM" of the embryo using PCR amplification of cancer cell specific nucleic acid sequences (FIG. 1).

It is an object of the present invention to provide a method for the identification of subjects possessing a cancer with an increased metastatic potential. The present invention relates to evaluation of metastatic potential by detecting the ability of a subject's cancer cells to intravasate blood vessels using the model assay system of the present invention. The detection and measurement of tumor cell intravasation across a blood vessel membrane constitutes a novel strategy for prognosis of cancer.

The present invention achieves a highly desirable objective, namely providing a method for the prognostic evaluation of subjects with cancer and the identification of subjects exhibiting a predisposition to developing metastatic cancer.

Specifically, the invention encompasses a method for determining the metastatic potential of cancer cells derived from a cancer subject comprising:

(a) introduction of a cancer cell sample derived from a cancer subject onto the upper chorioallantoic membrane of an avian embryo into which an artificially generated air pocket has been created;

(b) incubation of the embryo for a time sufficient to allow intravasation to occur; and (c) detection of migration of cancer cells from the upper chorioallantoic membrane to the lower chorioallantoic membrane, wherein a detection of cancer cells in the lower chorioallantoic membrane is an indicator of cancer cells with metastatic potential The assay system of the invention can also be used to monitor the efficacy of potential anti-cancer agents during treatment For example, the metastatic potential of cancer cells can be determined before and during treatment. The efficacy of the agent can be followed by comparing the metastatic potential of the cancer cells throughout the treatment. Agents exhibiting efficacy are those which are capable of decreasing the level of detectable cancer cells in the lower chorioallantoic membrane of the chick embryo.

The assay of the invention involves the creation of an artificially generated air sac in the upper CAM of the chick embryo into which cancer cells are inoculated. As an important component to the assay is the CAM, any hard shelled egg may be used including avian eggs of chickens, ducks, geese pheasants, quail, etc. In addition reptilian eggs may be used in the claimed assay. In the process of air sac generation, the upper CAM is wounded resulting in parts of the chorionic epithelium and basement membrane being damaged. Such damage, exposes loose vascularized stromal tissue. Cancer cells will enter this tissue regardless of their metastatic potential, but only those cells capable of penetrating the blood vessel walls will circulate and appear in the lower CAM. Cells which may be inoculated into the CAM of the embryo include but are not limited to cancer cell lines and cells derived from the tumor of a mammal, including cells derived from the tumor of a cancer subject, i.e., biopsied tumor tissue, etc.

Once the cancer cells have been inoculated into the upper CAM of the embryo, the embryo is incubated for a time sufficient to allow intravasation to occur. The inoculation time will vary depending on the metastatic potential of the inoculated cancer cells. In a preferred embodiment of the invention, the embryos are permitted to incubate for at least approximately 32 hrs at 37°.

Following incubation, migration of cancer cells from the upper CAM to the lower CAM of the embryo is detected using a variety of different methods. For example, the cancer cells may be detected in the lower CAM of the embryo through detection of cells expressing specific cell surface markers, i.e., cancer cell specific cell surface markers, in the lower CAM. The detection of cells expressing specific cell surface marker may be accomplished using a variety of different methods well known to those skilled in the art including but not limited to fluorescence microscopy or fluorescent activated cell sorting (FACS).

Alternatively, lower CAM cell lysates may be analyzed for the presence of proteins specifically expressed in cancer cells, but absent in chick embryo cells. Such differentially expressed proteins may be detected using, for example, inununoassays wherein the presence of cancer cell specific proteins are detected by the interaction with a specific antibody. Immunoassays useful in the practice of the invention include but are not limited to assay systems using techniques such as Western blots, radioimmunoassays and ELISA assays.

In a preferred embodiment of the invention, PCR amplification of cancer cell specific DNA sequences is carried out to detect the migration of inoculated cancer cells into the lower CAM. DNA sequences specific for the organism from which the cancer cells were derived may be amplified. In a preferred embodiment of the invention, DNA repeat sequences specific for the organism from which the cancer cells were derived may be used to selectively amplify cancer cell DNA but not embryo cell DNA. Such sequences, include but are not limited to repeat sequences such as human Alu sequences, specific genes such as actin or globin genes, or sequences specifically expressed in cancer cells.

5.1. In Vivo Screening Assay for Identification of Anti-Intravasation Agents The present invention further provides a screening assay for identification of agents capable of inhibiting the spread of cancer cells from a primary tumor to a site of metastasis formation via intravasation. In accordance with the invention, agents may be screened for their ability to inhibit intravasation of cancer cells. In utilization of the assay of the invention for purposes of identifying anti-metastatic agents, the test agent is co-inoculated with cancer cells. The migration of cancer cells into the lower CAM in the presence of a test agent is compared to the migration of cells in the presence of a vehicle control, wherein an anti-metastatic agent is identified as one capable of inhibiting the migration of cancer cells from the upper CAM into the lower CAM.

Specifically, the invention comprises a method for identifying an agent that inhibits intravasation of cancer cells comprising:

(a) introduction of a cancer cell sample and either a test agent or a vehicle control onto the upper chorioallantoic membrane of an avian embryo into which an artificially generated air pocket has been created;

(b) incubation of the embryo for a time sufficient for intravasation to occur; and (c) detecting the migration of cancer cells from the upper chorioallantoic membrane to the lower chorioallantoic membrane, wherein a decrease in the number of cancer cells detected in the lower chorioallantoic membrane in the presence of the test agent, as compared to the number of cancer cells detected in the presence of a vehicle control, identifies a compound that inhibits intravasation. In addition to co-introduction of the test agent and cancer cells onto the upper CAM, the test agent may be injected into the yolk sac or a blood vessel of the embryo.

The agents which may be screened in accordance with the invention include, but are not limited to inorganic compounds, peptides, antibodies and fragments thereof, and other organic compounds (e.g., peptidomimetics) that are capable of inhibiting the spread of cancer cells from a primary tumor to a site of metastasis formation. Agents may include, but are not limited to, peptides such as, for example, soluble peptides, including but not limited to members of random peptide libraries; (see, e.g., Lam, K. S. et al 1991, Nature 354:82–84; Houghten, R. et al., 1991, Nature 354:84–86), and combinatorial chemistry-derived molecular library made of D- and/or L-configuration amino acids, phosphopeptides (including, but not limited to, members of random or partially degenerate directed phosphopeptide libraries; see, e.g., Songyang, Z. et. al., 1993, Cell 72:767–778).

Agents identified via assays such as those described herein may be useful, for example, in defining the properties of cancer cells that enable successful intravasation, and for inhibiting metastasis formation in cancer subjects. Assays for testing the efficacy of compounds identified in the screens can be tested in animal model systems for tumor formation. Such animal models may be used as test substrates for the identification of drugs, pharmaceuticals, therapies and interventions which may be effective in treating cancer metastasis.

The assay of the invention may also be used to screen for nucleic acid sequences capable of inhibiting the metastatic potential of cancer cells. Such nucleic acid molecules include molecules comprising protein coding sequences or anti-sense sequences. Alternatively, nucleic acid molecules that competitively bind to specific cellular proteins may be assayed for their ability to inhibit intravasation. The nucleic acid molecules may be transferred to cancer cells prior to assaying by such methods as electroporation, lipofection, calcium phosphate mediated transfection, or viral infection.

5.2. Compositions and Uses

The present invention provides for treatment of proliferative disorders such as cancer, by administration of agents that regulate the metastatic activity of cancer cells. Compounds that may be administered to subjects with cancer include those agents identified using the assays described in Section 5.2., supra.

In a specific embodiment of the invention, the assay system of the invention was used to identify key proteases required for intravasation. For example, marimastat, which is an inhibitor of MMP-1, MMP-2, MMP-3, MMP-7 and MMP-9 with $IC_{50}$ of 1–20 nM, was tested for its ability to inhibit intravasation. In particular, 50 μl of 50–200 μM inhibitor, (FIG. 11) which, when equilibrated in the in chick embryo tissues (total weight of ~50 μm), should produce, a final concentration of 50 to 200 nM was tested for ability to inhibit intravasation. 100 μM marimastat (final 100 nM) produced the most pronounced inhibition of intravasation reducing the number of intravasation cells by 90%.

Transfection into cancer cells of a vector expressing antisense RNA for the urokinase plasminogen activator receptor (uPAR) reduced the surface expression of uPAr by 50%–70%. Additionally, such transfected cells exhibited a dramatically reduced ability to intravasate compared to cells transfected with the vector alone.

Inhibitors of proteolytic enzymes such as plasminogen activator, metalloproteinases and cathepsins, may be administered to inhibit the spread of cancer cells from a primary tumor to a site of metastasis formation. As demonstrated in the working example, an inhibitor of metalloproteinases (MMPs) was capable of inhibiting cancer cell intravasation by 90%. Cancers involving metastasis of tumor cells to other locations in the body are treated by administration of an agent that inhibits intravasation. Such cancers include, for example, lymphoma, solid tumors such as sarcomas and carcinomas, breast cancer and prostate cancer.

Compounds identified for use in prevention of intravasation can be tested in suitable animal model systems prior to testing in humans, including but not limited to rats, mice, chicken, cows, monkeys, rabbits, etc. For in vivo testing, prior to administration to humans, any animal model system known in the art may be used.

In specific embodiments, compounds that inhibit intravasation are administered to a subject having cancer where it has been determined that the subject's cancer cells have an increased metastatic potential. The increased metastatic potential can be readily detected, e.g., by obtaining a patient tissue sample (e.g., from biopsy tissue) and assaying for intravasation using the novel assay system of the present invention.

The invention provides methods of treatment of cancer by administration to a subject of an effective amount of a compound that inhibits intravasation. In a preferred aspect, the subject is an animal, and is preferably a mammal, and most preferably human.

The present invention also provides pharmaceutical compositions. Such compositions comprise a therapeutically effective amount of the compound capable of regulating the intravasation of cancer cells, and a pharmaceutically acceptable carrier. In a specific embodiment, the term "pharmaceutically acceptable" means approved by a regulatory agency of the Federal or a state government or listed in the U.S. Pharmacopeia for other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

6. EXAMPLE: IN VIVO ASSAY FOR MEASURING INTRAVASATION

The following example describes the use of a chick embryo CAM system, in combination with a PCR based assay, for measuring the metastatic potential of cancer cells. As demonstrated below, the metastatic potential of cancer cells correlated with the intravasation potential of the cells. Further, it was demonstrated that marimastat, an inhibitor of metalloproteinases, was capable of inhibiting the intravasation of cancer cells.

6.1. Materials and Methods

6.1.1 Reagents

Tissue culture media, glutamine and antibiotics were purchased from GIBCO Laboratories (Grand Island, N.Y.); trypsin from ICN Pharmaceuticals Inc. (Costa Mesa, Calif.); fetal bovine serum from JRH Biosciences (Lenexa, Kans.); gelatin from porcine skin, collagenase type 1A, BSA, fibronectin and heparin from Sigma Chemicals (St. Louis, Mo.); acidic fibroblast growth factor from Collaborative Research (Bedford, Mass.); chromogenic substrate for plasminogen, Spectrozyme PL from American Diagnostica (Greenwich, Conn.); human serum type A (heat inactivated) was prepared from platelet poor plasma, human plasminogen was purified from fresh frozen human plasma, DNA Isolation Systems from Oncogene Research products (Cambridge, Mass.) for initial experiments and Puregene from Gentra (Minneapolis, Minn.); Amplitaq Gold Taq Polymerase from Perkin Elmer (Branchburg, N.J.); dNTPs from New England Biolabs, Boston Mass.); $^{32}$P-adCTP and $^{125}$-IUdR from New England Nuclear (Boston, Mass.); COFAL-negative embryonated eggs from Specific Pathogen-Free Avian Supply (SPAFAS) (Norwich, Conn.); PCR primers and probes were from Genelink Inc. (Thornwood, N.Y.). Collagenase inhibitor BB2516 (Marimastat) was a generous gift from British Biotechnology Pharmaceuticals Ltd. The following human cells or cell lines were used: epidermoid carcinoma (HEp3); estrogen receptor negative (MDAMB231) and positive (MCF-7) breast cancer cell lines; androgen receptor negative (PC3) and positive (LNCaP) prostate cancer cell lines, fibrosarcoma (HT1080) and human embryo fibroblasts (HEF), a gift from Dr. E. L. Wilson, Cape Town, S.A. HEp3, HT1080 and HEF were cultured in Dulbecco's modified MEM with 10% heat inactivated FBS, (HI-FBS); MDAMB23 1, MCF-7, PC3, LNCAP were cultured in RPMI with HI-FBS, for MDAMB231 and MCF-7 cells the medium was supplemented with 5 $\mu$g/ml of insulin. HEp3 transfected with LK444 (vector control, designated clone LK 25) or HEp3 cells transfected with LK444 vector expressing antisense uPAR-RNA (AS-24, 33, 36 and 48) and in which surface uPAR was reduced by up to 70% were described previously (Yu et al., 1997, J. Cell Biol. 137:767–777).

6.1.2. In Vivo Experiments

For intravasation, invasion and tumor passage experiments chick embryos were obtained at 8 days of gestation and were maintained at 37° C. in a humidified, rotating incubator from Lyon Electronic Company, Inc.(Chula Vista, Calif.). HEp3 cells, AS-clones and LK 25 vector control clone were maintained in vivo by serial weekly passage of tumor fragments.

6.1.3. Intravasation

For intravasation experiments, the HEp3 tumors were dissociated with collagenase as described (Ossowski and Reich, 1980, Cancer Res. 40:2300–2309), plated at high density (3×10$^6$ cells per 100 mm dish) and passaged once 24 to 48 hrs prior to the experiment. Cultured cells used for intravasation were also passaged 24 to 48 hrs prior to experiment. Cells were detached from the culture dish with 2 mM EDTA in PBS, counted, resuspended in 50 $\mu$l of PBS with Ca$^{++}$ and Mg$^{++}$ and inoculated (usually at 10$^6$ cells, unless indicated otherwise) onto a CAM of a 9 day old chick embryo in which an artificial air sac was created (designated "upper CAM" see FIG. 1). After 50 hrs of incubation (unless specified otherwise) the lower half of the CAM (designated "lower CAM", FIG. 1) was removed, placed in a sterile 14 ml polypropylene tube, the tissue was snap-frozen in liquid nitrogen and stored frozen at −80° C. For the time dependence experiment, the cells were inoculated inside 8 nm inner diameter sterile Teflon rings (removed from 1.8 ml freezing vials, Nunc, Denmark). This prevented leaking and spreading of cells when the "lower CAMs" had to be removed early (5 min, 6 hrs) after inoculation. To test for inhibition by marimastat (BB 2516), HEp3 cells were prepared as above but one group was resuspended in PBS with Ca$^{++}$ and Mg$^{++}$, while two others were resuspended in 100 or 200 $\mu$M inhibitor in PBS with Ca$^{++}$ and Mg$^{++}$. The cells were inoculated inside Teflon rings and the inhibitor re-applied 24 hrs later.

6.1.4. Intravenous Injection

Cells prepared as above (using EDTA in PBS for detachment) were resuspended at 1–2×10$^5$ per 50 $\mu$l of PBS containing Ca$^{++}$ and Mg$^{++}$ and using 28 gauge hypodermic needles injected intravenously into 10.5 day old chick embryos, prepared by opening a small "window" in the egg shell, but without dropping the CAM, such that the CAM vessels were easily accessible for injection. At 4 hrs the "lower CAM" was removed, snap-frozen and used to extract genomic DNA.

6.1.5. Preparation of Chicken and Human Endothelium and Adhesion Studies

Human umbilical vein endothelium (HUVEC) was prepared as described (Jaffe, 1984, Culture and Identification of Large Vessel Endothelial Cells. In Biology of Endothelial Cells, E. A. Jaffe, ed. (Boston: Martinus Nijhott Publishers, Kluwer Academic Publishers Group), pp. 1–13) and grown on dishes pre-coated with fibronectin (50 μg/ml) in medium M199 with 20% human serum, 50 μg/ml heparin and 100 ng/ml of bFGF. Chick endothelium was prepared from blood vessels of 15 day old chick embryos using a miniaturized HUVEC preparation method, and grown under the same conditions as HUVEC except that the medium was supplemented with 30% human serum and 1% egg yolk. For experiments, the endothelial cells were plated at $1.5 \times 10^4$ cells per well in a 24 well tray and incubated in full medium for 3 to 4 days, washed and incubated for 24 hrs in growth; yolk was not added to chick endothelium. Tumor cells labelled for 20 hrs with $^{125}$-IUdR were washed extensively, detached, resuspended at $1 \times 10^4$ cells/ml and 0.5 ml of Dulbecco's medium with 10 mM HEPES and 1 mg/ml BSA and inoculated into wells with endothelium. The trays were rotated at 60 rpm at 37° C. for 10 min, the floating cells aspirated, the monolayers washed 3 times, and the remaining cells solubilized in 1N NaOH and counted in a γ-counter. Adhesion of tumor cell to endothelium is expressed as % of radioactivity (cpm) in the inoculum.

6.1.6. Growth of Cancer Cells on CAM

After an artificial air sac was formed, cancer cells growing in tissue culture were inoculated on CAMs at $5 \times 10^5$ or $2 \times 10^6$ cells per CAM, on 3 to 4 CAMs each. After 1week of incubation, nodules or tumors formed at the site of inoculation were excised, weighed, minced, and inspected microscopically for the presence of cancer cells. The mince of small nodules was reinoculated on fresh CAMs for two consecutive weeks.

6.1.7. DNA Extraction and Human Alu-Sequence PCR Amplification

The frozen tissue were crushed in lysis buffer with sterile 5 ml pipettes. Genomic DNA was isolated from "lower CAMs" using DNA Isolation Kit (Gentra Systems) as per manufacturer's specifications. Specific primers for human Alu sequences were Alu-Sense: 5' ACG CCT GTA ATC CCA GCA CTT 3' (SEQ ID NO: 1) and Alu-Antisense: 3' TCG CCC AGG CTG GAG TGC A 5' (SEQ ID NO: 2) which produced a band of 224 bp. The primers were positioned in the most conserved areas of the Alu-sequence (Kariya et al., 1987, Gene 53: 1–10) (first monomer, nt 21–40, and in the second monomer, nt 263 -245). The PCR was performed under the following conditions: 95° C. for 10 mn, 95° C. for 30 sec, 58° C. for 45 sec, 72° C. for 10 min. The reaction mixture contained 1 μg of genomic DNA as template, 1×PCR buffer, 1.5 mM $MgCl_2$, 50 μm dNTPs, 1.0 μM each of Alu Sense and Antisense primers, 1–2 Units of Amplitaq Gold, 0.1 μCi fresh $^{32}$P-α-dCTP. The PCR products were electrophoresed on a 7% polyacrylamide gel at 100V for 1 hr, dried and exposed to film at –80° C. The bands were quantitated by densitometric scanning using GelScan XL (Pharmacia, Upsala, Sweden).

6.1.8. Protease Assays: uPA Assay

Cells were plated in 6-well trays and grown to near confluence, the medium was removed and the cells were washed and incubated with 2 ml of serum-free medium for 24 hrs. The medium was collected, centrifuged, and frozen until assayed. The cells were lysed in 300 μl of 0.1 M Tris pH 8.1 and 0.1% Triton X-100. The uPA (10 μl of conditioned medium and 10 μg of cell protein) was assayed as previously described (Mira y Lopez and Ossowski, 1987, Cancer Res. 47, 3558–3564), using plasminogen and chromogenic plasminogen substrate.

6.1.9. Gelatin Gel Zymography

Ten μl aliquots of conditioned media were electrophoresed at 4° C. on 8% PAGE containing 0.1% gelatin, the gel washed in 2.5% Triton X-100 for 30 min, rinsed in water, and incubated for 40 hrs at 37° C. in buffer containing 50 mM Tris pH 7.7, 5 mM $CaCl_2$, and 0.02% $NaN_3$. To test for inhibition of MMPs by BB2516, HEp3 cell conditioned medium was electrophoresed in quadruplicate. The gel was cut into 4 fragments each containing one sample (lane) and incubated separately as above except that marimastat was added in increasing concentration to the incubation buffer. All gels were stained with Coomassie blue, de-stained and dried between dialysis sheets.

6.2 Results

6.2.1. PCR-Amplification of Human Alu-Sequences-Sensitivity and Specificity of the Method Prior to quantitating human cancer cells in vivo, a standard curve was constructed by mixing uninoculated CAMs with increasing numbers of cancer cells, extracting the DNA and using aliquots of 1 μg of DNA as a template in a PCR amplification of human Alu-sequences. Because the reaction mixture contained $^{32}$-P labeled dCTP, following separation of the PCR products on PAGE, the resultant bands could be autoradiographed and quantitated by scanning densitometry. When the mix contained between 50 and 800 cancer cells per CAM, a strong band of the expected size of 220 bp was amplified (FIG. 2A); with >800 cancer cells in the mix larger fragments of variable sizes were amplified. Fifty cells per CAM (FIG. 2A) is equivalent to 1 human cell in $2 \times 10^6$ host cells, a level of sensitivity achieved because of the high content of Alu-sequences present in human genomic DNA (Kariya et al., 1987, Gene 53:1 –10). FIG. 2B, in which densitometric units were plotted against corresponding numbers of cancer cell added to the CAMs, shows that within at least 1.5 log range there is a direct relationship between the intensity of the bands and the number of cancer cells present in the mix. (Only the 220 bp band was used for quantitation). If predetermined experimental conditions (number of PCR cycles and the amount of radioactive nucleotide added) are kept constant, the standard curve (FIG. 2B) can be used to extrapolate the numbers of human tumor cells present in unknown samples.

Mixtures of mouse and human genomic DNA could also be analyzed in a similar way, and although the background was slightly greater than with chick tissue, it was possible to produce specific, easily recognizable bands that could be densitometrically scanned (FIG. 3) expanding the potential use of this method to nude or SCID mice.

6.2.2. Dose and Time Dependence of Intravasation

The dose-dependence of intravasation was tested by inoculating CAMs with increasing (0.5 to $2.0 \times 10^6$) numbers of cells and quantitating the cells arrested in the vasculature of the "lower CAM" (FIG. 1), a compartment physically connected to the site of inoculation only through blood and lymphatic vessels. As shown in FIGS. 4A and 4B, one of the two embryos inoculated with the lowest ($0.5 \times 10^6$) number of cells, had ~50 intravasated cells, the other one was negative. (In 3 additional experiments in a total of 6 eggs, 2 embryos had ~50 cells (limit of detection), the rest were negative. "Lower CAMs" of embryos inoculated with either 1 or 2×10⁶ HEp3 cells were always positive, and the number of cells was proportional to the inoculum.

To determine the time dependence of intravasation, CAMs were inoculated with 1×10⁶ HEp3 cells and DNA was extracted from "lower CAMs" at 5 min and 6, 16, 24, 32 and 54 hr. No cancer cells were found in the "lower CAMs" harvested at 5 min to 24 hrs post-inoculation, indicating that either no intravasation has taken place or that the number of cells arrested during the 24 hrs was <50 or <0.005% of the inoculum (FIG. 4C). These results also indicated that this assay, rather then measuring passive entry of cancer cells into injured blood vessels, measures an active process of intravasation. The number of intravasated cells found 54 hr after inoculation was, as determined from the reconstruction curve (FIG. 2B) 4 to 5 fold greater than after 32 hrs. This increase was mostly due to continuous seeding of cancer cells from the primary site and, to a much lesser degree, due to cell division. That intravasation is an active process is further supported by the observation that, not only dissociated single cells, but fragments of HEp3 tumors, containing a similar number of cancer cells display a comparable degree of intravasation (FIG. 4D) which appears to proceed with similar kinetics. This observation for direct testing of surgical cancer specimens for their ability to intravasate.

6.2.3. Intravasation by Cancer Cells of Dissimilar Malignant Potential

Pairs of cancer cell lines of high and low malignant potential, originating from breast (MDAMB231 and MCF-7) and prostate (PC3 and LNCaP) carcinomas, and a fibrosarcoma (HT1080) and primary human embryo fibroblasts (HEF) pair were compared for their ability to intravasate; malignant HEp3 cells served as a positive control. FIG. 5A, which is a composite of 3 individual experiments in which intravasation by MDAMB231, HT1080 and PC3 cells was compared to that of HEp3 cells, shows that these 3 cell lines, chosen for their recognized greater malignant potential, intravasate as efficiently as HEp3 cells. In contrast, MCF-7, HEF and LNCaP cells appear incapable of intravasation. The inability of MCF-7 and HEF cells to intravasate was not remedied by extending the assay to up to 5 days (FIG. 5B), which dramatically increased the number of intravasated HEp3 cells.

6.2.4. Properties of Cancer Cells Unable to Invade Blood Vessel Walls

Reduced ability of certain cell to invade the blood vessel wall would drastically diminish the number of cells entering the circulation. Furthermore, a defect in adhesion to endothelium would cause re-circulation and death of cancer cells due to shearing stress, while an inoculum of cells with reduced proliferative capacity would provide a relatively smaller pool of cells capable of intravasation. All of these may result in lesser number of cells detected in the "lower CAM". To bypass the potential difference in the ability of cells from different origin to breach the blood vessel wall, cells were delivered by intravenous injection. (The number of cells injected was 2×10⁵ or less, since larger inocula of some of the cell types were previously found to be lethal, results not shown). Each of the cell types tested, including normal human fibroblasts, was detected in the "lower CAM" 4 hrs (FIG. 6) and 24 hrs after intravenous injection. Thus, it appears that differences in adherence to endothelium and/or cell capillary trapping cannot explain the differences in the level of cell detected in the "lower CAM". This conclusion was confirmed by showing that under conditions mimicking the shearing stress exerted on tumor cells in the circulation, HEp3 cells with vastly different ability of intravasation were equally capable to adhere to chick and human endothelium, (FIG. 7). That this interaction was similar for both chicken and human endothelium, suggests that at least at this level, the chick embryo is a good model for testing human tumor cells.

To exclude the possibility that the high intravasation capacity of some cell lines is due to their high proliferation rate in vivo, we tested their growth by inoculating 0.5×10⁶ cells per CAM and incubating the inoculated embryos for a week. For cells that did not produce tumors in this time period, the inoculum was increased to 2×10⁶ cells per CAM. Table 1 shows that only HEp3 and HT 1080 grew progressively on CAMs forming large (~400 mg) tumors.

TABLE 1

Production of uPA, and growth in vivo.

| Cells | uPA U/1 × 10⁶ cells/24 hr | Growth on CAM |
|---|---|---|
| HEp3 | 1.8 | + + +[a] |
| MDAMB231[b] | 2.3 | +/−[b] |
| MCF-7[b] | Undetected. | +/−[b] |
| PC3[b] | 2.6 | +/−[b] |
| LNCaP[b] | Undetected. | +/−[b] |
| HT1080[a] | 2.1 | + + + |
| HEF | 0.9 | NT |

[a]Inoculum of 5 × 10⁵ cells per CAM; [b]inoculum of 1 × 10⁶ cells per CAM. uPA was measured by a chromogenic assay (see Materials and Methods) in serum-free conditioned media collected over a 24 hr period. Growth on CAM was determined 1 week after cell inoculation and in two subsequent passages in vivo: + + + represent tumors >200 mg which, when re-inoculated on CAMs, continue to produce large tumors; +/− represent very small nodules, <40 mg. Tumor cells can be discerned microscopically in mince of these nodules.

Neither breast nor prostate cancer cell lines, including the two (MDAMB23 1 and PC3) which intravasated as efficiently as HEp3, produced tumors on CAMs. (Small nodules were evident at the site of inoculation of all cells, but they did not increase in size even after 2 additional in vivo passages). Thus, in the short (50 hrs) time period required to complete the intravasation assay, proliferation rate had a negligible effect on the number of cells found in the lower CAM. These results led us to conclude that the actual breaching of the blood vessel wall had to be considered as the rate limiting step.

6.2.5. The Effect of Reduced Surface Proteolysis on Intravasation

Since evidence links cancer cell urokinase plasminogen activator (uPA) and metalloproteinases (MMPs) with degradation of extracellular matrix protein and invasion (see Mignatti and Rifkin, 1993, Physiol. Rev. 73:161–194 for review) it was tested whether these enzymes played a crucial role in invasion of the blood vessels and thus intravasation. uPA production was high in all cells that intravasated efficiently, but also in HEF cells (see Table 1), which did not intravasate at all, suggesting that uPA may be necessary but not sufficient to accomplish this task. To test its role more directly, intravasation of 4 clones of HEp3 cells, in which surface uPAR was reduced by up to 70% through transfection of a vector expressing antisense RNA (Yu et al., 1997, J. Cell Biol. 137:767–777), was compared to that of parental HEp3 cells or a clone of HEp3 cells transfected with vector alone (FIG. 8). The intravasation of cells with low uPAR, and thus low surface uPA, was drastically reduced or completely blocked. This result shows that surface uPA/uPAR are indispensable for intravasation.

The examination of conditioned media in a gelatin zymography assay of all cells tested for intravasation revealed varied profiles of metalloproteinases (MMPs); some (MCF-7) with no detectable MMPs, and others (HEp3 and MDAMB23 1) with 3 (MMP-1,2 and 9) MMPs (FIG. 9).

as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims. Various publications are cited herein that are hereby incorporated by reference in their entireties.

```
                               SEQUENCE LISTING

<160> NUMBER OF SEQ ID NOS: 2

<210> SEQ ID NO 1
<211> LENGTH: 21
<212> TYPE: DNA
<213> ORGANISM: Human

<400> SEQUENCE: 1
acgcctgtaa tcccagcact t                                                    21

<210> SEQ ID NO 2
<211> LENGTH: 19
<212> TYPE: DNA
<213> ORGANISM: Human

<400> SEQUENCE: 2
tcgcccaggc tggagtgca                                                       19
```

To test whether inhibition of MMPs interferes with the process of intravasation we used a water soluble MMP-inhibitor, marimastat. In an in vitro assay using a zymogran of HEp3 conditioned medium as a source of MMPs, the inhibitor at 80 nM concentration was sufficient to block most of the MMP-9 and all of the MMP-1 activity. A residual lysis zone of MMP-2 was present even when 1.6 $\mu$M was used (FIG. 10). We tested the effect of the inhibitor on intravasation of HEp3 cells in vivo by mixing it with the inoculum and re-applying the inhibitor to the site of inoculation after 24 hr. As shown in FIG. 11, 50 $\mu$l of 100 $\mu$M marimastat which, if distributed evenly throughout the embryo and the extra-embryonic tissues, should yield a final concentration of 100 nM, reduced the number of intravasated cells by more than 90%. In a separate experiment we found that even a final concentration of 50 nM was sufficient to produce more than 60% inhibition of intravasation; a higher inhibitor concentration (200 $\mu$M, FIG. 11) was less effective. Individually, these results can not identify the specific MMP responsible for intravasation. However, the results in FIG. 9, showing that of the 7 cell lines tested only the 4 which express MMP-9 activity are capable of intravasation, points to MMP-9 as the crucial enzyme. FIG. 12 shows that the low-expressing uPAR-clones (AS 24 and 33), a vector control and the parental HEp3 cells, all produce activity corresponding to MMP-9, yet clones AS 24 and AS 33 intravasate very poorly (FIG. 8), indicating that a combination of MMP-9 and surface uPA/uPAR is crucial for intravasation.

The present invention is not to be limited in scope by the specific embodiments described herein, which are intended

What is claimed is:

1. A method for determining the metastatic potential of cancer cells derived from a cancer subject comprising:
    (a) introducing a cancer cell sample derived from a cancer subject onto an upper chorioallantoic membrane of an avian embryo into which an artificially generated air pocket has been created;
    (b) incubating the embryo for a time sufficient to allow intravasation to occur; and
    (c) detecting migration of cancer cells from the upper chorioallantoic membrane to a lower chorioallantoic membrane,
wherein the detection of cancer cells in the lower chorioallantoic membrane is performed using a polymerase chain reaction and detection of cancer cells in the lower chorioallantoic membrane is an indicator of cancer cells with metastatic potential.

2. The method of claim 1 wherein the cancer cells are biopsied tumor cells.

3. The method of claim 1 wherein the polymerase chain reaction amplifies a human specific DNA fragment.

4. The method of claim 3 wherein the human specific DNA fragment comprises human ALU repeat sequences.

5. A method for identifying an agent that inhibits intravasation of cancer cells comprising:
    (a) introducing a cancer cell sample and either a test agent or a vehicle control onto an upper chorioallantoic membrane of an avian embryo into which an artificially generated air pocket has been created,
    (b) incubating the embryo for a time sufficient for intravasation to occur; and
    (c) detecting migration of cancer cells from the upper chorioallantoic membrane to a lower chorioallantoic membrane, wherein the detection of cancer cells in the lower chorioallantoic membrane is performed using a polymerase chain reaction and a decrease in the number of cancer cells detected in the lower chorioallantoic membrane in the presence of the test agent, as compared to the number of cancer cells detected in the presence of a vehicle control, identifies a agent that inhibits intravasation.

6. The method of claim 5 wherein the polymerase chain reaction amplifies a human specific DNA fragment.

7. The method of claim 6 wherein the human specific DNA fragment comprises human ALU repeat sequences.

8. A method for identifying a nucleic acid molecule that inhibits intravasation of cancer cells comprising:

(a) introducing the nucleic acid molecule into a cancer cell sample;

(b) introducing of the cancer cell sample onto an upper chorioallantoic membrane of an avian embryo into which an artificially generated air pocket has been created;

(b) incubating of the embryo for a time sufficient for intravasation to occur; and (c) detecting migration of cancer cells from the upper chorioallantoic membrane to a lower chorioallantoic membrane, wherein the detection of cancer cells in the lower chorioallantoic membrane is performed using a polymerase chain reaction and a decrease in the number of cancer cells detected in the lower chorioallantoic membrane in the presence of the nucleic acid molecule, as compared to the number of cancer cells detected in the absence of the nucleic acid molecule, identifies a nucleic acid molecule that inhibits intravasation.

9. The method of claim 8 wherein the nucleic acid molecule is an antisense molecule.

* * * * *